(12) United States Patent
Staton (10) Patent No.: US 11,325,129 B2
(45) Date of Patent: May 10, 2022

(54) SWAB COLLECTION KIT

(71) Applicant: OXOID LIMITED, Basingstoke (GB)

(72) Inventor: John Marshall Staton, Waltham, MA (US)

(73) Assignee: OXOID LIMITED, Basingstoke (GB)

( * ) Notice: Subject to any disclaimer, the term of this patent is extended or adjusted under 35 U.S.C. 154(b) by 195 days.

(21) Appl. No.: 16/096,755

(22) PCT Filed: Apr. 21, 2017

(86) PCT No.: PCT/US2017/028752
§ 371 (c)(1),
(2) Date: Oct. 26, 2018

(87) PCT Pub. No.: WO2017/189346
PCT Pub. Date: Nov. 2, 2017

(65) Prior Publication Data
US 2019/0118172 A1    Apr. 25, 2019

Related U.S. Application Data

(60) Provisional application No. 62/329,257, filed on Apr. 29, 2016.

(51) Int. Cl.
*B01L 3/00*       (2006.01)
*A61F 13/38*     (2006.01)
(Continued)

(52) U.S. Cl.
CPC ........ *B01L 3/5029* (2013.01); *A61B 10/0045* (2013.01); *A61B 10/0096* (2013.01);
(Continued)

(58) Field of Classification Search
CPC .... B01L 3/5029; B01L 1/52; B01L 2300/042; B01L 2300/047; B01L 2300/0816;
(Continued)

(56) References Cited

U.S. PATENT DOCUMENTS 3,013,656 A    12/1961  Murphy, Jr.
3,519,123 A     7/1970  Nagle et al.
(Continued)

FOREIGN PATENT DOCUMENTS

EP         0223745           5/1987
EP         0223745 A1 *      5/1987    .......... A61M 35/006
(Continued)

OTHER PUBLICATIONS

JPS5836384A Machine English Translation Description (Year: 1983).*
(Continued)

*Primary Examiner* — Michael L Hobbs
*Assistant Examiner* — Lenora A Abel
(74) *Attorney, Agent, or Firm* — BakerHostetler (57) ABSTRACT

A collection system including a storage tray and a swab positioned in the storage tray, wherein the swab is configured to collect a sample comprising one or more microorganisms. The system further includes a generally elongate storage device positioned in the tray. The storage device is configured to contain a culture medium therein and configured to receive therein at least part of the one or more microorganisms collected by the swab. The storage tray includes a first recess configured to receive the storage device in a longitudinal configuration, and a second recess configured to receive the storage device in an axial configuration oriented generally perpendicular to the longitudinal configuration.

19 Claims, 9 Drawing Sheets

(51) Int. Cl.
*B65D 1/36* (2006.01)
*A61B 50/33* (2016.01)
*A61B 10/02* (2006.01)
*A61B 10/00* (2006.01)
*A61B 50/30* (2016.01)
*C12M 1/12* (2006.01)
*C12M 1/00* (2006.01)
*C12M 3/00* (2006.01)
*A61B 50/00* (2016.01)
*B01L 1/00* (2006.01)

(52) U.S. Cl.
CPC .............. *A61B 10/02* (2013.01); *A61B 50/30* (2016.02); *A61B 50/33* (2016.02); *A61F 13/38* (2013.01); *B65D 1/36* (2013.01); *C12M 23/06* (2013.01); *C12M 23/38* (2013.01); *C12M 23/54* (2013.01); *A61B 2010/0216* (2013.01); *A61B 2050/0065* (2016.02); *A61B 2050/3008* (2016.02); *B01L 1/52* (2019.08); *B01L 2300/042* (2013.01); *B01L 2300/047* (2013.01); *B01L 2300/0816* (2013.01); *B01L 2300/0832* (2013.01)

(58) Field of Classification Search
CPC . B01L 2300/0832; A61B 50/30; A61B 50/33; A61B 10/0045; A61B 10/0096; A61B 10/02; A61B 2050/0065; A61B 2050/3008; A61B 2010/0216; A61F 13/38; B65D 1/36; C12M 23/06; C12M 23/38; C12M 23/54
USPC ...................................................... 435/307.1
See application file for complete search history.

(56) References Cited

U.S. PATENT DOCUMENTS

| | | | |
|---|---|---|---|
| 3,924,741 A | | 12/1975 | Kachur et al. |
| 4,085,845 A | * | 4/1978 | Perfect ................ B65D 81/133 206/564 |
| 4,170,300 A | * | 10/1979 | Pick ....................... A61B 50/33 206/365 |
| 4,803,048 A | * | 2/1989 | Nason ................ A61B 10/0096 422/401 |
| 5,449,071 A | | 9/1995 | Levy |
| 2013/0164738 A1 | * | 6/2013 | Becker ............... C12N 15/1006 435/6.1 |
| 2014/0243706 A1 | | 8/2014 | El-Fahmawi |
| 2014/0360903 A1 | | 12/2014 | Iio et al. |

FOREIGN PATENT DOCUMENTS

| | | | | |
|---|---|---|---|---|
| EP | 0420450 | | 4/1991 | |
| EP | 0420450 A1 | * | 4/1991 | ............ B01L 3/5029 |
| JP | S5836384 A | * | 3/1983 | |

OTHER PUBLICATIONS

European Patent Application No. 17790147.7; Extended Search Report; dated Oct. 29, 2019; 9 pages.

International Search Report and Written Opinion issued in parent PCT/US2017/028752, dated Jul. 17, 2017.

International Patent Application No. PCT/US2017/028752; Int'l Preliminary Report on Patentability; dated Nov. 8, 2018; 10 pages.

* cited by examiner

SWAB COLLECTION KIT

This application is the National Stage Application of International Patent Application No. PCT/US2017/028752 filed Apr. 21, 2017, which claims the benefit of U.S. Provisional Application No. 62/329,257, filed Apr. 29, 2016, the entireties of which are incorporated by reference.

Collection kit for providing swabs and culture medium.

One embodiment of a sterile swab collection system or kit 10 is shown in FIGS. 1-5, 7 and 8 which can be useful for clinical, veterinary, industrial and environmental applications. The swab collection system 10 can provide one more swabs and a medium for transport, preservation and/or culture or microorganisms (collectively referred to herein as "culture medium"), and be used to obtain samples of microorganisms so that the microorganisms can be collected, incubated, tested and/or analyzed. In one case the system 10 can be used to test swabbed samples for the presence of antibiotic resistant microorganisms, such as Methicillin-resistant *Staphylococcus aureus* ("MRSA"), Vancomycin-resistant enterococci ("VRE"), and Carbapenenem-resistant enterobacteriaceae ("CRE"), but the system 10 and its use thereof is not limited to such use.

Figure 2:
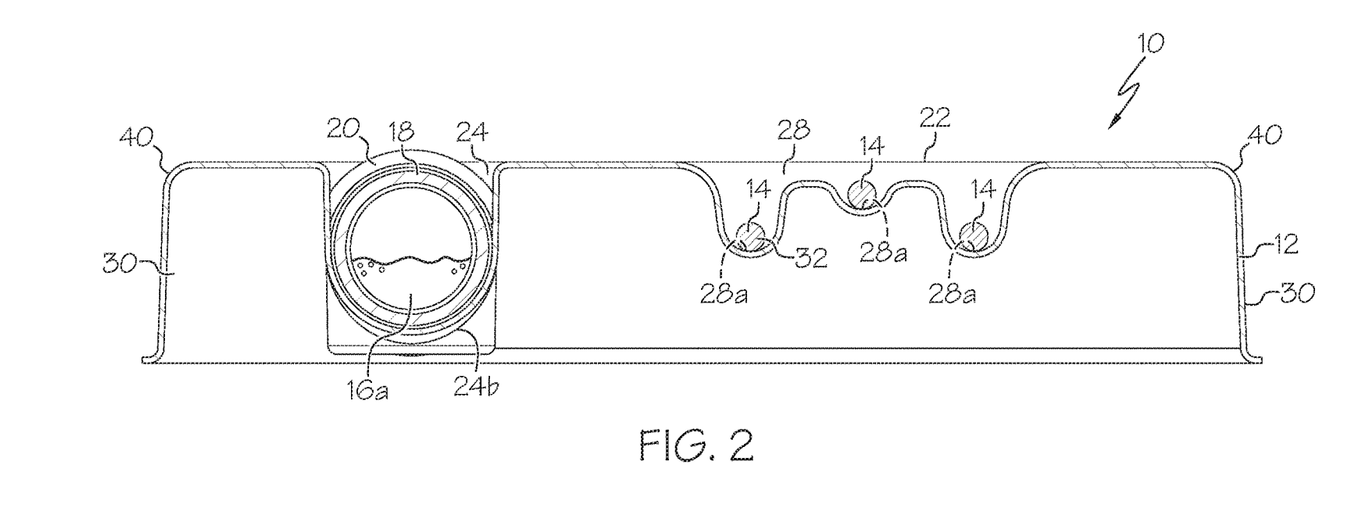
FIG. 2 is a side cross section of the system of FIG. 1, taken along line 2-2 of FIG. 1.
Figure 3:
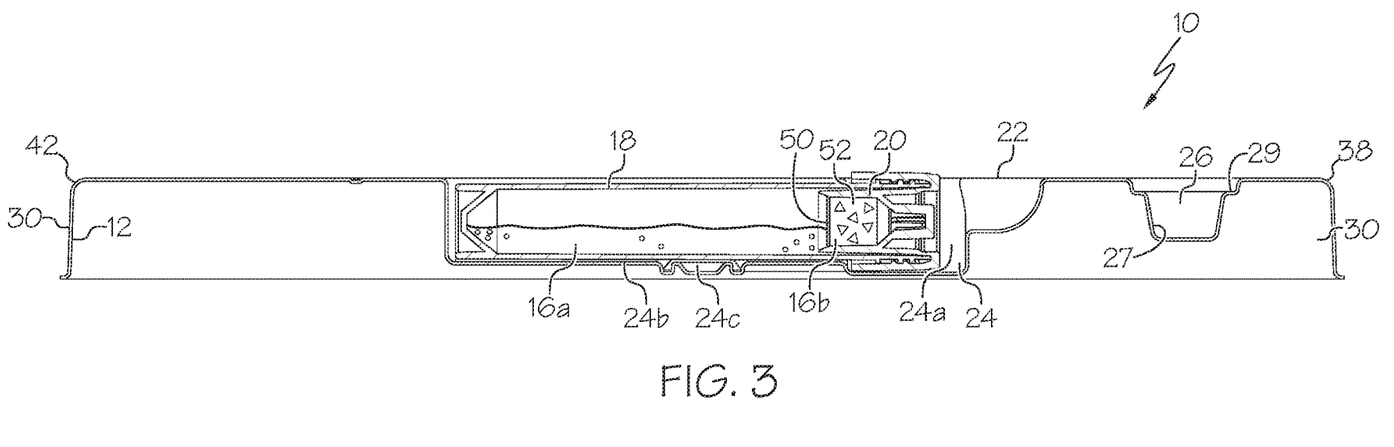
FIG. 3 is a side cross section of the system of FIG. 1, taken along line 3-3 of FIG. 1.
Figure 4:
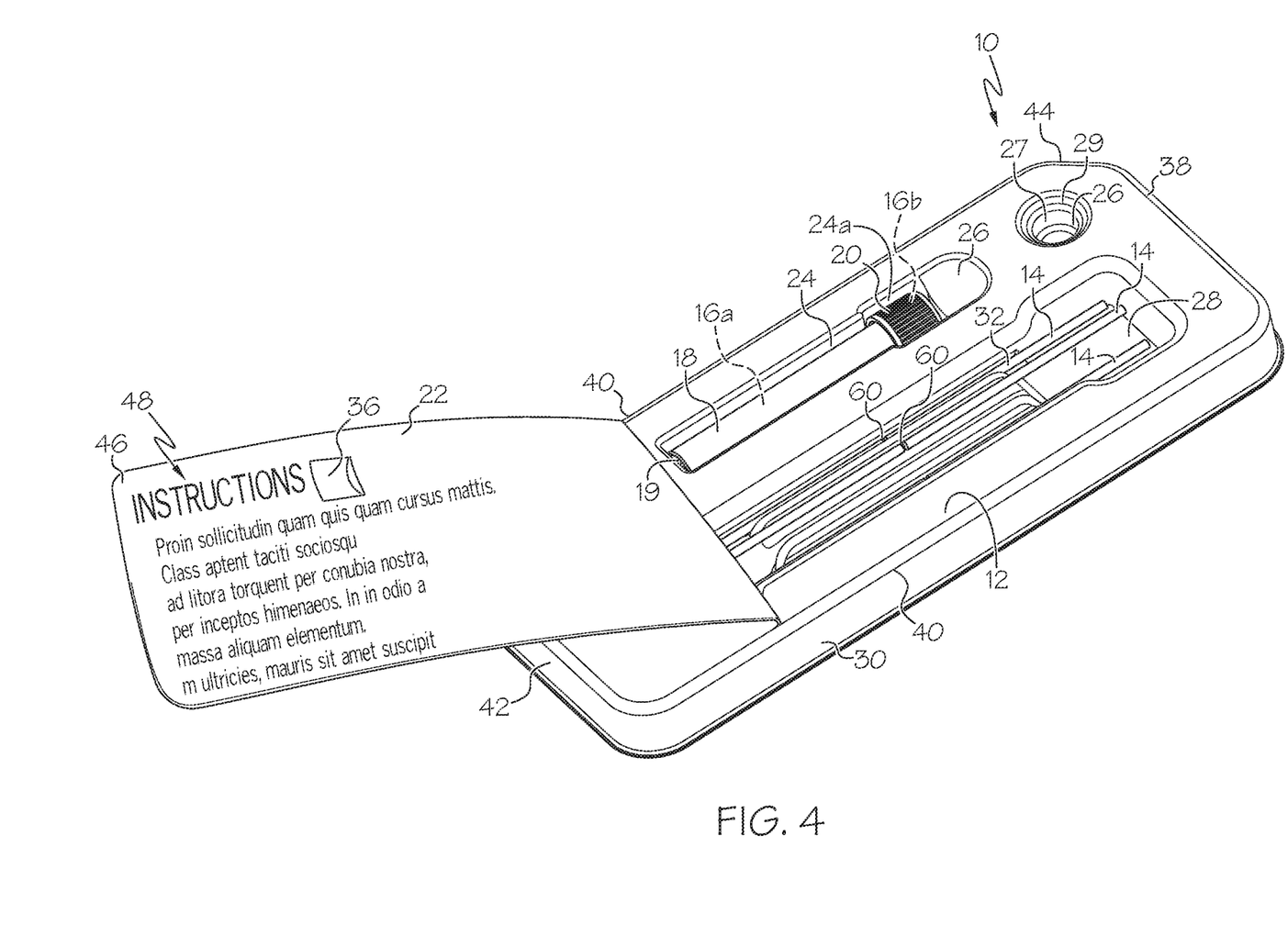
FIG. 4 illustrates the collection kit of FIG. 1 with the cover partially peeled back.

The collection system 10 can include, generally speaking, a storage tray 12, one or more swabs 14, a culture medium 16, a storage device 18, and a cap 20, all of which can be positioned in the storage tray 12 in various configurations, for example as shown in FIGS. 2-4. In this manner the storage tray 12 provides a structural framework for storing and protecting the components 14, 16, 18 and 20. The storage tray 12 can include and/or be coupled to a cover 22, in the form of a peelable film in one case, as will be described in greater detail below. The tray 12 and cover 22 can each be generally flat and planar.

The tray 12 can be made of a relatively thin, lightweight yet durable material, such as polymers, and configured to receive and store the various components 14, 16, 18 and 20 therein. In particular, the tray 12 may include various recesses formed or molded therein to store various components, including a storage device recess 24, a cap receiving recess 26, and a swab receiving recess 28. The bottom surfaces of the recesses 24, 26, 28 extend from the underside thereof to provide a base upon which the tray 12 can rest when positioned on a tabletop or the like in a horizontal configuration. However, in one embodiment the tray 12 can include a skirt 30 extending downwardly from an upper surface of the tray 12 and extending entirely, or nearly entirely, around an entire perimeter of the tray 12 to provide a stable surface upon which the tray 12 can rest.

The system 10 can include one or multiple swabs 14 positioned therein. In the illustrated embodiment each swab 14 includes a generally, elongate rigid stem 32 which can be made of a variety of materials such as polymers, wood, flocked fiber as disclosed in U.S. Pat. No. 8,317,728, etc. Each swab 14 also includes a tip or portion 34 made of absorbent material, such as cotton, fabrics, polymers, etc. Each tip 34 can be sufficiently absorbent to collect an adequate sample for culture, or if multiple swabs 14 are used, to collectively provide an adequate sample for culture such that, in one case for example, each tip 34 can absorb at least one time its weight in water, and in another case up to five times its weight in water.

Figure 1:
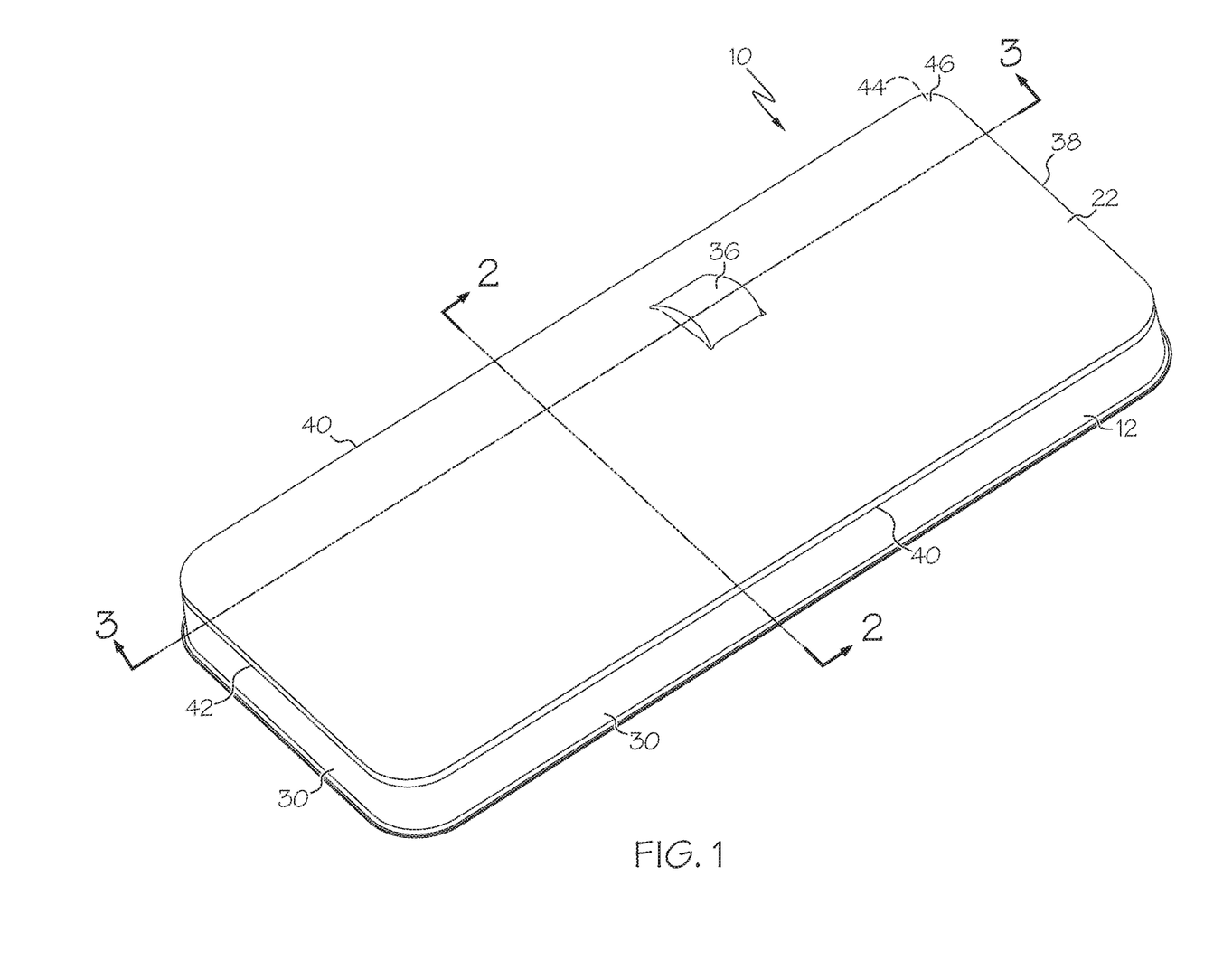
FIG. 1 is an upper perspective view of one embodiment of the collection kit, shown in a closed configuration.

In order to use the system 10, the system 10 may be shipped and received in the condition shown in FIGS. 1-3, wherein the components 14, 16, 18 and 20 are entirely received in the tray 12, and the cover 22 is sealingly coupled to the storage tray 12 about an entire perimeter thereof to protect the components 12, 14, 16, 18 and 20 and prevent contamination thereof. In the illustrated embodiment the system 10 is shipped such that the cap 20 is coupled to the storage device 18 and both are stored on their sides in a longitudinal configuration. In this case the cap 20 is stored in the storage device recess 24, which can include an enlarged portion 24a to receive the cap 20. In addition the cover 22 can also include a cap-receiving expansion portion 36 to accommodate the cap 20.

The cover 22 can be coupled to the tray 12 by a relatively weak adhesive about a distal edge 38 and at least part of the side edges 40 adjacent the distal edge 38 of the tray 12 to enable part of the cover 22 to be manually peeled away/separated from the tray 12, as shown in FIG. 4. This adhesive may be relatively weak and allow separation of the cover 22 from the tray 12 by manual forces. However, a portion of the cover 22 (e.g., along the base edge 42 and/or remaining/adjacent portions of the side edges 40) can be secured with a relatively strong adhesive which prevents further manual peeling/removal of the cover 22 without damaging the tray 12 and/or cover 22. Such portions of the cover 22 can be secured to the tray 12 by means of various adhesives or other means, such as heat sealing, mechanical fasteners, etc., which are stronger than the adhesive used to removably secure portions of the cover 22.

Figure 5:
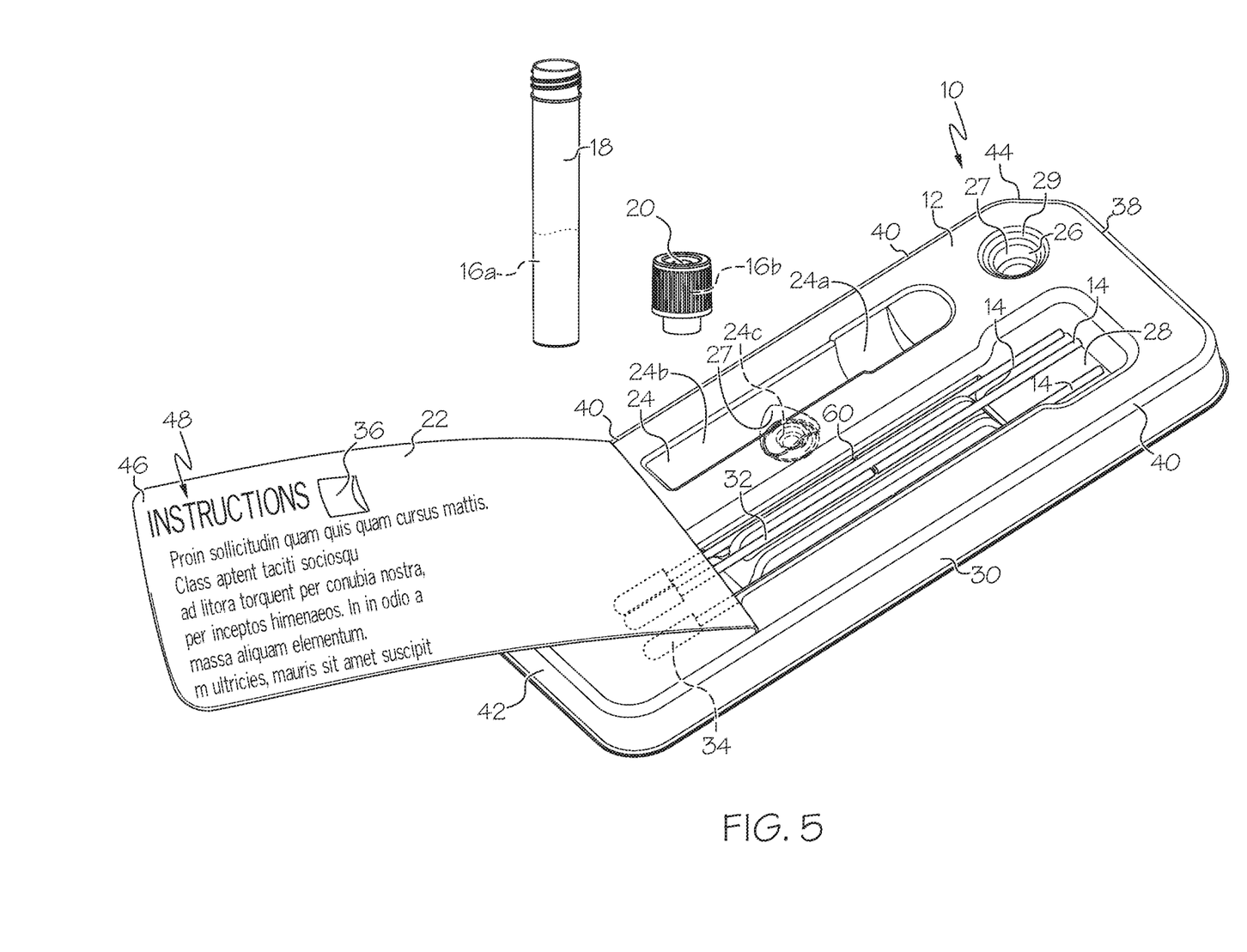
FIG. 5 illustrates the collection kit of FIG. 4 with the storage device and cap removed.

The portions of the cover 22 which are permanently and/or more securely coupled to the tray 12 are positioned adjacent to and/or cover the absorbent portion 34 of the swabs 14 as shown in FIG. 5. In this manner, the cover 22 is manually manipulable to expose (e.g. in a direction perpendicular to a plane of the tray 12) at least part of the swab(s) 14 (e.g. the stems 32), but is not manually manipulable to expose the absorbent portion 34 of the swab(s) 14, when the swabs 14 are positioned as stored/shipped. This arrangement helps to ensure the absorbent tips 34 of the swab(s) 14 remained covered/protected to limit and/or prevent direct physical contact of any spilled fluids, dropped components, etc., with the tips 34 to reduce contamination. However, when the cover 22 is partially removed as shown in FIG. 4 the cap 20 and/or storage device 18 may be entirely or generally entirely exposed such that a user can access those components.

The tray 12 can include a notch 44 at a corner thereof which exposes portions of the overlying cover 22 to provide a gripping portion 46 where a user can grip and pull the cover 22, exposing the contents of the tray 12. The cover 22 can thus include a gripping portion 46 which extends beyond a perimeter of at least part of the tray 12 which is engaged by the cover 22 (e.g. the upper lip) when the cover 22 is in its closed position (FIG. 1). In addition, usage instructions 48 for the system 10 may be positioned on the underside of the cover 22 (FIG. 5). In this manner, the instructions 48 are positioned to be immediately observable by the user when the cover 22 is peeled back. In addition, the non-removable nature of the cover 22 helps to ensure that the instructions 48 are not separated from the tray 12 and thus inadvertently discarded or lost.

Once the cover 22 is retracted, it may next be desired to prepare the storage device 18 for receipt of samples. The storage device 18 can take the form of a generally elongate cylindrical or tubular device with an inner volume therein, wherein the cap 20 is threadably attached to the storage device 18 as shipped. The storage device 18 can include an outer ring 19 extending about its lower perimeter (see FIGS. 11-14). The storage device recess 24 can include a first portion or first recess 24b configured to receive the storage device 18 in a longitudinal configuration wherein an axis of the storage device 18 is generally parallel to a plane of the tray 12/cover 22. A bottom surface of the portion 24b can be semi-circular or other portions of a circle in end view (for example when the storage device 18 is cylindrical in shape as shown), or other shapes as necessary to conform to the storage device 18.

Figure 7:
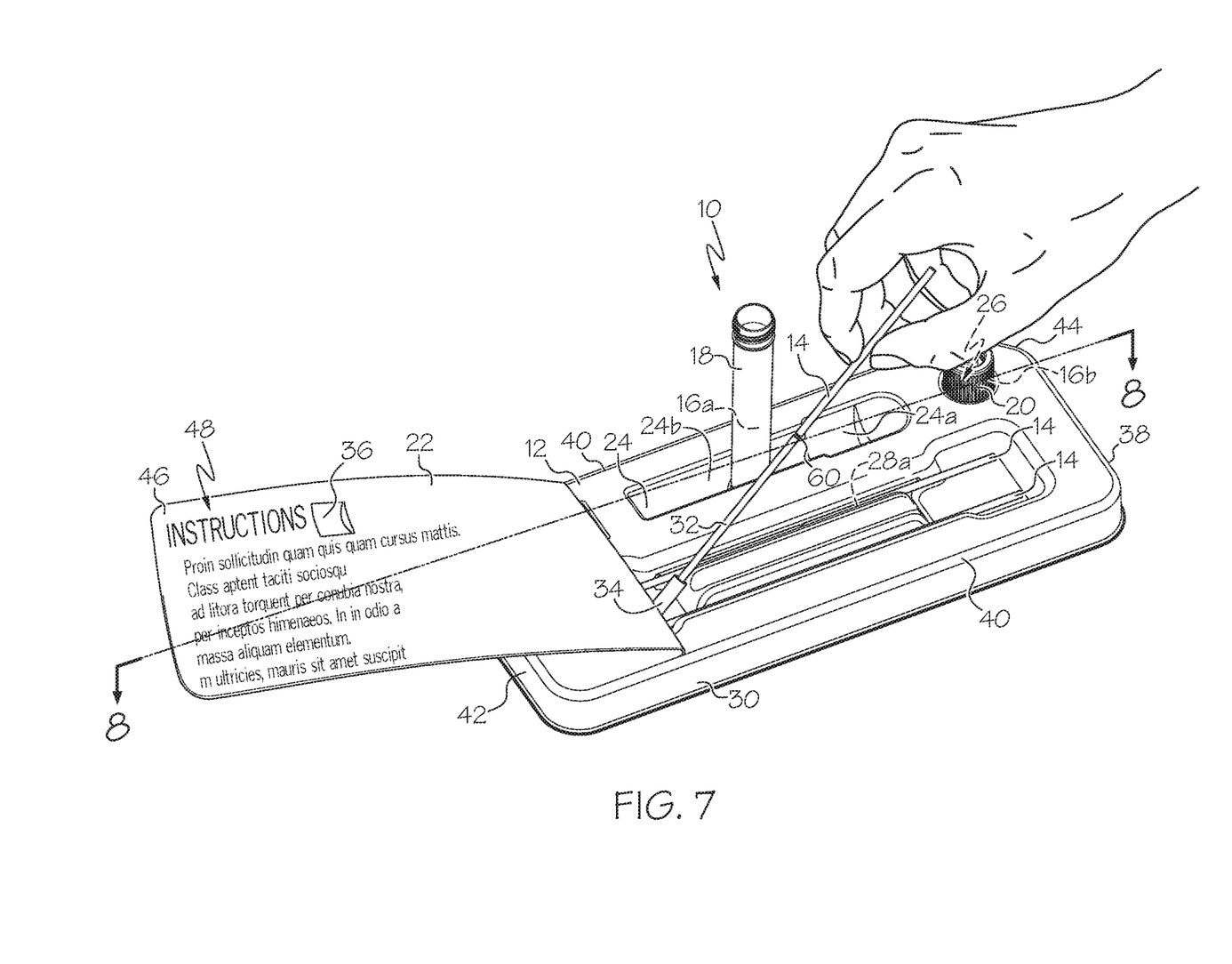
FIG. 7 illustrates the collection kit of FIG. 5 with the storage device and cap placed in the storage tray and a swab being manually removed.
Figure 8:
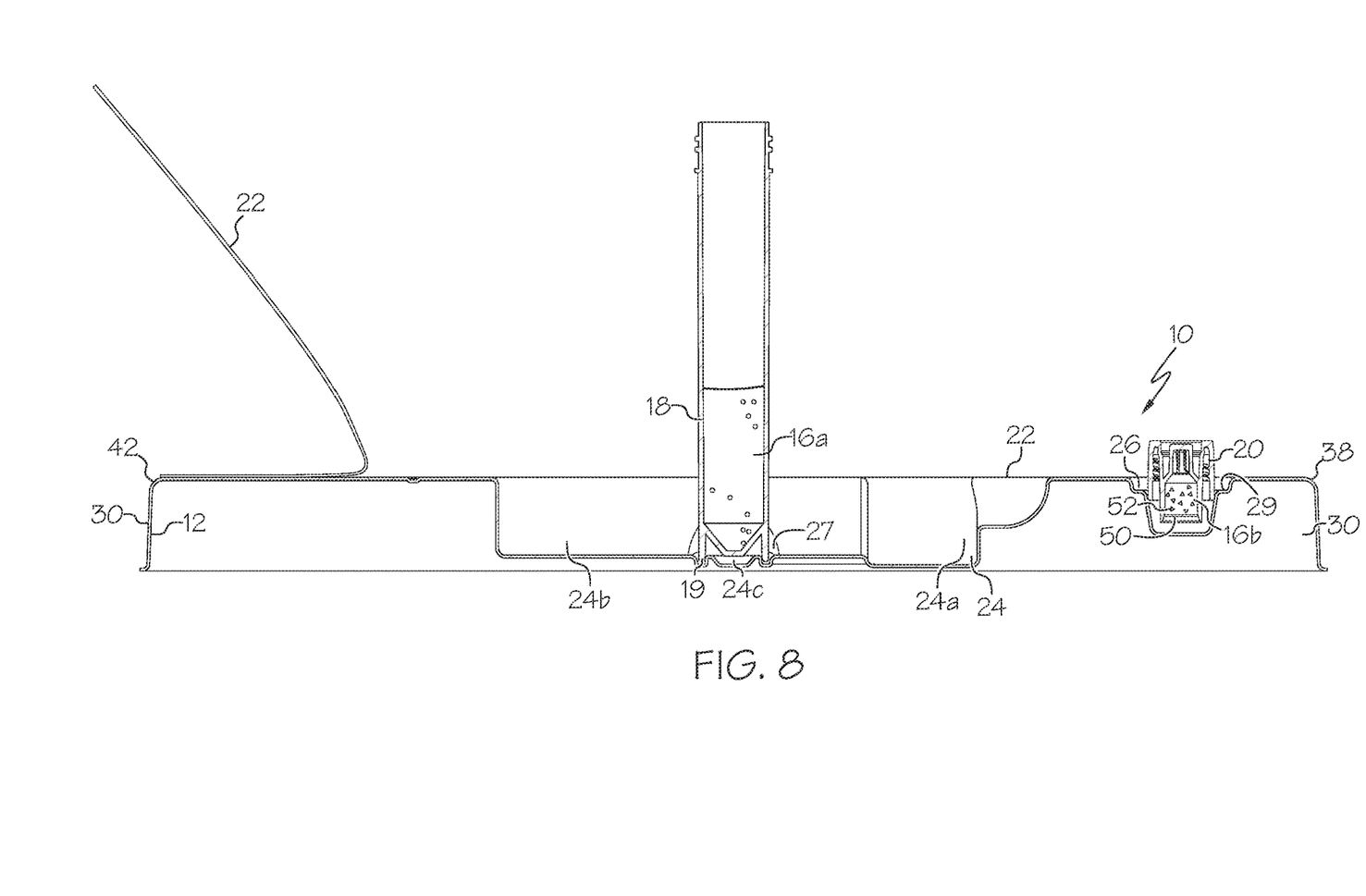
FIG. 8 is a side cross section of the system of FIG. 7, taken along line 8-8 of FIG. 7.
Figure 9:
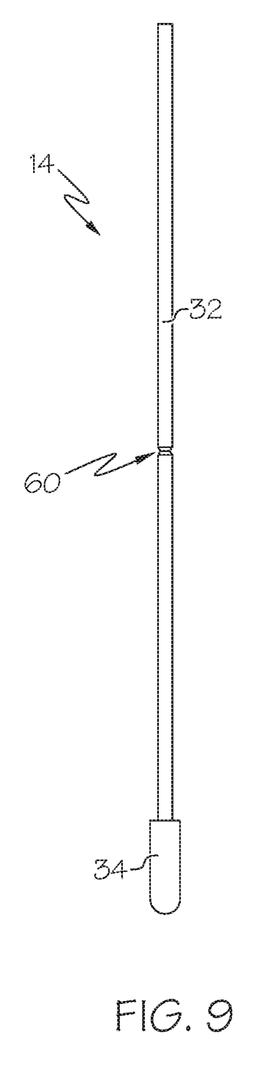
FIG. 9 is a front view of a swab which can be used with the system of FIGS. 1-5 and 7.
Figure 10:
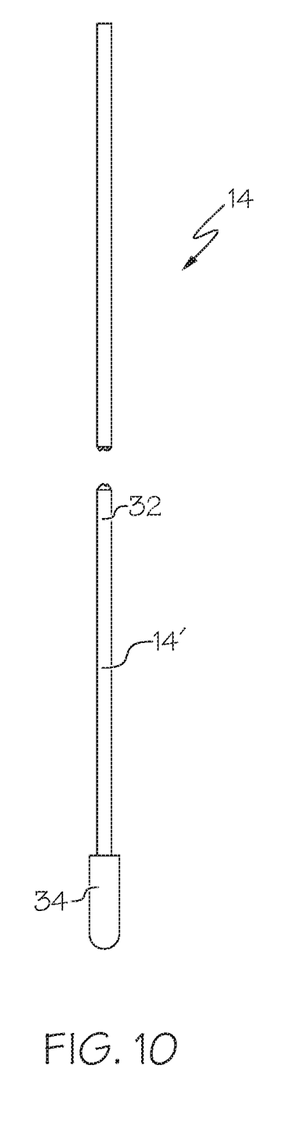
FIG. 10 illustrates the swab of FIG. 9 broken along a break line.
Figure 11:
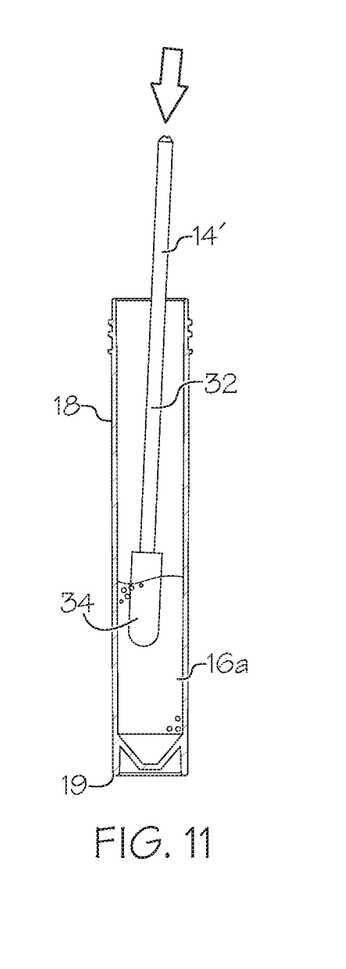
FIGS. 11-14 are a series of views showing the swab segment of FIG. 10 inserted into a storage device.

The cap-receiving recess 26 can be positioned adjacent to the storage device recess 24. The cap 20 is storable in the cap-receiving recess 26 as shown in FIG. 7. The cap 20 can be generally cylindrical, and is threadably attachable to the storage device 18. The cap-receiving recess 26 can have tapered side walls 27 and/or an internal circumferentially-extending ledge or lip 29 on the tapered side walls 27, as shown in FIG. 3, and be configured such that the cap 20 can rest upon the ledge 29, or alternatively, the cap 20 can be gripped within the tapered side walls 27 in a wedging action, as shown in FIG. 8. In this case the cap 20 is positioned in the cap-receiving recess 26 but spaced away from a bottom of the recess 26 to protect/isolate a seal 50 positioned therein, even when the seal 50 is flush with a distal end 54 of the cap 20. The cap-receiving recess 26 may be generally conical, cylindrical or other shape to receive and hold the cap 20 in a manner that does not compromise the sterility of the cap 20.

Figure 6:
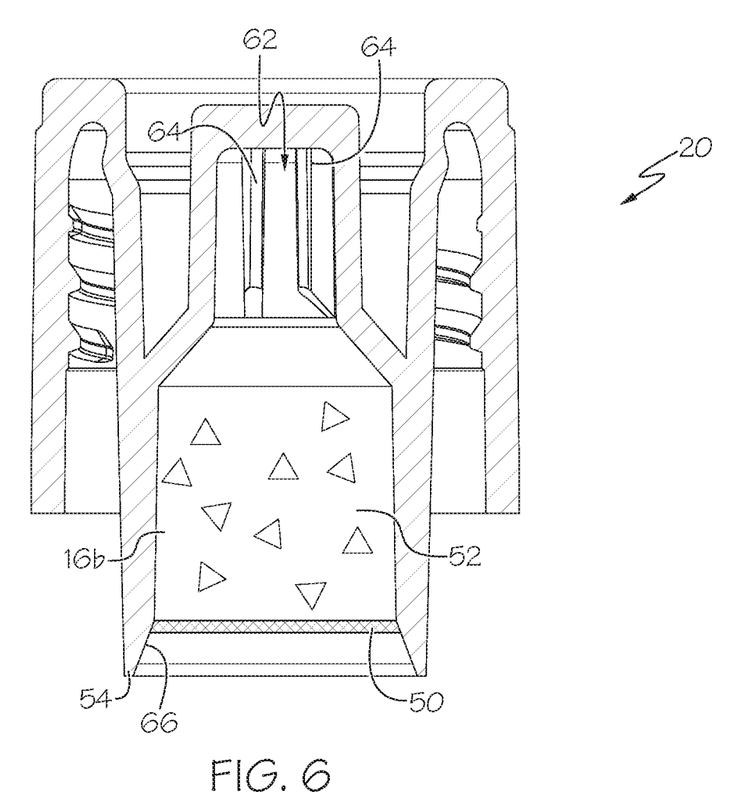
FIG. 6 is a side cross section of the cap of the system of FIGS. 1-5.

The storage device 18 and/or cap 20 can store the culture medium 16 therein. In the illustrated embodiment the culture medium 16 is split into two components: a liquid component or part 16a stored in the storage device 18, and a solid component or part 16b stored in the cap 20. As shown in FIG. 6, the cap 20 can include a sealing component 50, such as a sealing foil or the like, defining a sealed cavity 52 in the cap 20. The sealed cavity 52 and cap 20 thereby segregates the two portions 16a, 16b of the culture medium 16 when the system 10 is shipped as shown in FIGS. 1-3. The solid component 16b can be vacuum dried, lyophilized, or air-dried material, such as nutrients for consumption by microorganisms, antibiotics for selective growth of microorganisms, and/or reagents for detecting growth. The solid component 16b can, due to its dried nature and treatment, be positioned primarily around the outer rim of the sealed cavity 52, and in particular in an upper recess 62 thereof, but for illustrative purposes the solid component 16b is shown herein as being evenly distributed in the sealed cavity 52. The liquid portion 16a can provide a medium for dispersal of the solid component 16b and provide an environment for growth by microorganisms. It may be desired to separate the solid 16b and liquid 16a components until use and/or include a desiccant near the solid component 16b to prolong the shelf life of the culture medium 16.

As shown in FIG. 6, the sealing component 50 of the cap 20 is spaced axially away from a distal end 54 of the cap 20. In this manner, the sealing component 50 and/or sealed cavity 52 are spaced away from the distal end 54 of the cap 20 to help protect those components from touching any other components and from contamination. However, in some cases the sealing component 50 is not spaced away from the distal end 54, and may be generally flush with the distal end 54.

In order to use the system or kit 10 and proceed with securing samples, in one embodiment the storage device 18 and cap 20 can be removed from the storage device recess 24, and cap 20 can be separated from the storage device 18, as shown in FIG. 5. The cap 20 can be stored in the cap receiving recess 26, if desired, as shown in FIG. 7. After the storage device 18 is extracted from the tray 12 it can be stored in the tray 12 in a generally vertical configuration, as shown in FIG. 7. Next, the foil 50 in the cap 20 can be removed, pierced or otherwise compromised such that the solid component 16b of the culture medium 16 can be introduced into the storage device 18 and mixed with the liquid component 16a of the culture medium 16. After mixing, the cap 20 can be screwed into place on the storage device 18, and the storage device 18 can be shook to mix the solid 16b and liquid 16a components of the culture medium 16.

It should be understood that the solid 16b and liquid 16a components of the culture medium 16 can be segregated and/or introduced and mixed in a wide variety of manners. For example, in one case, the sealing component 50 is automatically pierced when the cap 20 is sufficiently screwed onto and/or secured to the storage device 18. In this case the solid portion 16b of the culture medium 16 is automatically released and introduced into the liquid portion 16a. In addition, it should be understood that the positions of the solid 16b and liquid 16a portions of the culture medium 16 can be reversed; that is, the liquid component 16a of the culture medium 16 can be positioned in the cap 20 and the solid component 16a positioned in the cavity of the storage device 18.

As outlined above, the storage device 18 may be desired to be positioned in a vertical position for storage and/or mixing, as shown in FIG. 7. The storage device recess 24 can include a second portion or second recess 24c which is configured to receive the storage device 18 in an axial configuration oriented generally perpendicular to when the storage device 18 is in its longitudinal configuration (i.e. stored in the first portion 24b of the storage device recess 24). The second portion 24c can be formed as or include an annular portion configured to closely receive a lower portion (i.e., ring 19) of the storage device 18 therein, as shown in FIG. 8. The second portion 24c can have radially-inward tapered side walls 27, as shown in FIGS. 5 and 8, analogous to the tapered side walls 17 of the cap receiving recess 26 shown in FIG. 3. The tapered side walls of the second portion 24c can thus be configured such that the storage device 18 can be gripped therein in a wedging action, as shown in FIG. 8. In this case the storage device 18 is securely positioned in the tray 12 and less prone to being knocked over, spilling its contents. In one embodiment the second portion 24c has a height/volume less than one-quarter, of a height/volume of the storage device 18, and in another case not greater than about one-half of a height of the storage device 18, to ensure the storage device 18 can be properly retained therein, but to avoid taking up excess space.

The first portion 24b can have a generally curved lowermost portion (a partial circle in cross section as shown in FIG. 2) with an axis oriented generally parallel to a plane of the tray 12/cover 22. The second portion 24c can have a generally curved portion (a complete circle in one case) with an axis oriented generally perpendicular to the plane of the tray 12/cover 22. The first 24b and second 24c portions can at least partially overlap in top view of the tray 12, and in one case the second portion 24c is entirely positioned within the first portion 24b in top view, to provide a space savings to the tray 12. The first 24b and second 24c portions can also each be considered separate recesses rather than part of the same recess 24.

With reference to FIG. 2, each of the swabs 14 can be separated in a lateral direction (i.e. in a plane parallel to a plane defined by the tray 12 and/or cover 22). In addition some or adjacent ones of the swabs 14 can be stored at differing height/thickness locations in a direction perpendicular to the lateral direction. The tray 12 thus can include multiple individual swab receiving recesses 28a at varying heights to store the swabs 14 at multiple/varying heights, which avoids interference between adjacent swabs 14 and increases ease of accessing the free, distal end of each swab 14. In particular, the vertical spacing of the swabs 14 enables a user to more easily fit his or her fingertip about the free end of the swab 14, and lift the swab 14 away from its individual swab receiving recess 28a while providing clearance in a 360 degree direction around each free distal end of the swab 14 as shown in, for example, FIG. 5.

After a swab 14 is removed from the tray 12, the swab 14 can be wiped/swabbed across a surface to be tested, for example, a surface or cavity of a human subject, to swab/absorb any microorganisms. The swab 14 is then introduced into the culture medium 16 in the storage device 18 to introduce the swabbed microorganisms into the culture medium 16. Additional swab(s) 14 can, if desired, then be utilized to wipe across a surface or cavity to absorb additional microorganisms and introduce the additional microorganisms into the culture medium 16. Such body sites and cavities include, without limitation, the armpit, groin, rectum, a wound, sore or infection site, nasal cavity and/or throat. Other applications, for example veterinary, industrial and, environmental uses, may involve swabbing of other surfaces including, without limitation, hospital beds, counter tops, drinking fountains, air ducts, food preparation areas and the like. One or more of the swabs 14 may be retained in the storage device 18 or one or more of the swabs 14 may be discarded after introducing the microorganisms into the culture medium 16. The cap 20 is then sealingly secured to the storage device 18, and the storage device 18 can then be transported and/or utilized for further culture and/or testing.

FIGS. 9-14 illustrate a particular optional method and structure for introducing the swabs 14 and/or solid 16b and liquid 16a portions of the culture medium 16 to each other. In particular, in the illustrated embodiment a swab 14 can have a break line or break portion 60 along which the swab 14 is predetermined to break. In one case, the stem 32 of the swab 14 can have a reduced thickness portion and/or be made of weakened materials, relative to other or adjacent portions of the stem 32. In any case, after swabbing is complete, the swab 14 can be broken along the break line 60, and the remaining portion of the swab 14' inserted into the storage device 18. The cap 20 can, with its seal 50 intact, then be screwed down onto the storage device 18.

Figures 12, 13:
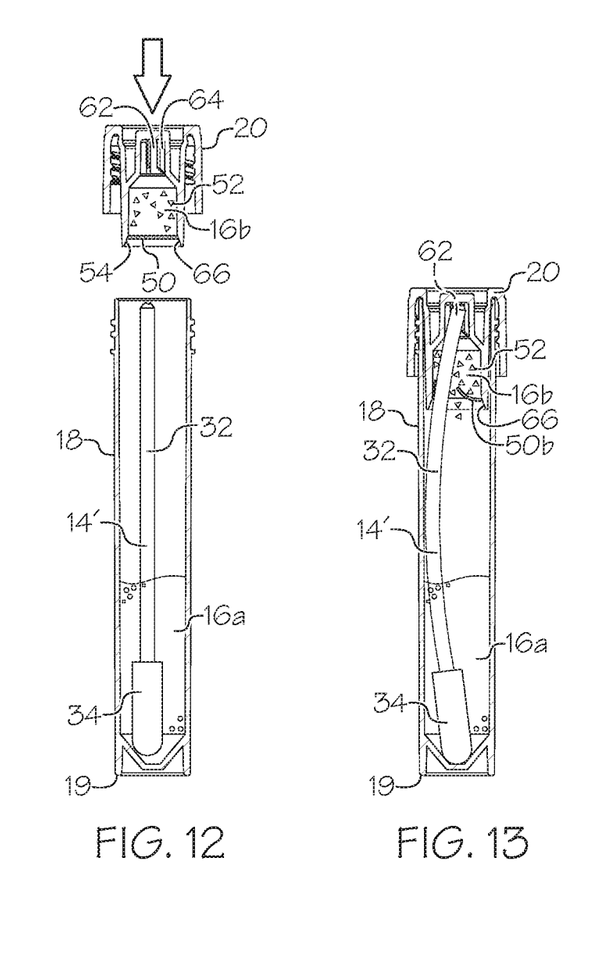
Figure 14:
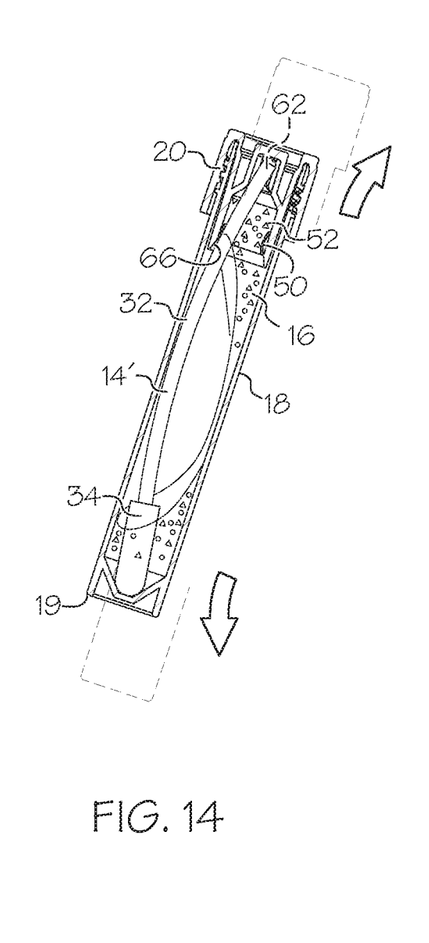

The swab portion 14' is sized such that the distal (broken) end of the swab portion 14' pierces the sealing component 50 when the cap 20 is secured to the storage device 18, enabling the solid portion 16b of the culture medium 16 to escape the sealed cavity 52 and enter the inner volume of storage device 18 (FIG. 13). Thus the components can be configured such that when the cap 20 is fully secured to the storage device 18 the sealing component 50 is spaced away from a distal (bottom) inner end of the storage device 18 by a predetermined distance. The broken swab 14' is configured to have a length greater than the predetermined distance to enable the seal 50 to be pierced. After the seal 50 is pierced and the solid portion 16b of culture medium 16 is introduced to the liquid portion 16a, the storage device 18 can then be shaken, as shown in FIG. 14, to mix the culture medium 16.

In addition, if desired, the cap 20 can include a recess 62 with gripping flanges 64 configured to closely receive and grip the distal end of the swab portion 14' therein. The cap 20 can include an angled surface 66 adjacent to the distal end 54 and configured to guide the broken swab 14' toward the seal 50 and recess 62 when the cap 20 is tightened down. In this manner when the cap 20 is separated from the storage device, the swab portion 14' remains coupled to the cap 20 such that the swab portion 14' can be easily discarded, and/or the saturated absorbent tip 34 of the gripped swab portion 14' can be used to transfer portions of the sampled microorganisms and/or culture medium 16. In addition the gripping flanges 64 provide fluid channels so that the liquid portion 16b can reach and mix with the solid portion 16a positioned in the recess 62. However, in some cases the cap 20 may not include the recess 62 and/or gripping flanges 64, and in some cases a swab 14 (or swab portion 14') may not be left in the storage device 18.

The broken swab 14' may in some cases have a length greater than a distance between an upper-most inner portion of the cap 20/recess 62 and a distal inner end of the storage device 18, when the cap 20 is begun to be secured to the storage device 18 and/or prior to when the cap 20 is entirely secured to the storage device 18. By having a swab portion 14' with this length, the swab portion 14' is bent/deformed when the cap 20 is secured to the storage device 18, as shown in FIG. 13. The bending/deformation ensures that the distal end of the swab portion 14' is positioned to one side of and not centered relative to the cap 20. This in turn ensures that the swab portion 14' pierces the seal 50 on one side, and not a center thereof. Thus, when the cap 20 is continued to be screwed into place, the swab portion 14' pierces/circumscribes the seal 50 about its entire perimeter thereof when the cap 20 is turned 360 degrees. This in turn ensures the seal 50 is completely opened to ensure proper mixing of the components 16a, 16b.

Having described the invention in detail and by reference to the various embodiments, it should be understood that modifications and variations thereof are possible without departing from the scope of the claims of the present application.

What is claimed is:

1. A collection system comprising:
   a storage tray having an upper surface, the upper surface having a perimeter;

a cover covering the upper surface and attached to the perimeter, said cover having a first portion that is attached and retractable from a first area of the perimeter and a second portion that is non-removably attached to a second area of the perimeter, wherein the first portion remains connected to the second portion when retracted from the first area of the perimeter;

a plurality of swabs positioned in a plurality of swab receiving recesses separated laterally within said storage tray, wherein at least two of said swab receiving recesses are positioned at different heights within the storage tray; each swab being configured to collect a sample comprising one or more microorganisms;

a generally elongate storage device positioned in said tray, said storage device being configured to contain a culture medium therein and configured to receive therein at least part of said one or more microorganisms collected by at least one of said plurality of swabs, wherein said storage tray includes a first recess configured to receive said storage device in a longitudinal configuration, and wherein said storage tray includes a second recess entirely positioned within said first recess and configured to receive said storage device in an axial configuration oriented generally perpendicular to said longitudinal configuration or in a horizontal position for the tubular section of said storage device, and a third recess to receive a cap of the storage device when said cap is removed from said storage device; and wherein the storage tray further includes a skirt extending downwardly from the upper surface and extending entirely or nearly entirely around a perimeter of the tray, said skirt providing support of the tray.

2. The system of claim 1 further comprising said culture medium positioned in said tray, said culture medium being configured to facilitate growth of microorganisms introduced to said culture medium.

3. The system of claim 2 wherein said culture medium includes a liquid component and a solid component that is isolated relative to said liquid component, said solid component consisting of a vacuum-dried, lyophilized, or air-dried material.

4. The system of claim 1 wherein at least part of said culture medium is positioned in said storage device.

5. The system of claim 1 further including said cap of the storage device positioned in said storage tray, wherein said cap is attachable to said storage device to seal said storage device.

6. The system of claim 5 wherein at least part of said culture medium is removably positioned in said cap.

7. The system of claim 6 wherein said cap includes a sealing component forming a sealed cavity in said cap in which said at least part of said culture medium is positioned, and wherein said sealing component is spaced away from a distal end of said cap.

8. The system of claim 6 wherein said cap includes a sealing component forming a sealed cavity in said cap in which said at least part of said culture medium is positioned, and wherein each swab includes a break line along which each swab is predetermined to break, and wherein said cap, each swab and said storage device are configured such that when each swab is broken along said break line and positioned in said storage device and said cap is attached to said storage device, each swab pierces said sealing component, wherein each swab includes a relatively rigid shaft and an absorbent portion at one end thereof.

9. The system of claim 8 wherein said plurality of swabs and said storage device are sealingly positioned in said tray, and wherein said cover is manually manipulable to expose at least part of said plurality of swabs, and wherein said cover is not manually manipulable to expose said absorbent portion of said plurality of swabs.

10. The system of claim 1 wherein said tray is generally flat and planar and said storage device includes a central axis, and wherein when said storage device is in said longitudinal configuration said axis is generally aligned with a plane of said tray and wherein when said storage device is in said axial configuration said axis is oriented generally perpendicular to said plane of said tray.

11. The collection system of claim 1 wherein each swab is configured to collect a sample comprising one or more microorganisms, wherein at least two of said plurality of swabs are separated in both a lateral direction and a height direction extending perpendicular to said lateral direction.

12. The collection system of claim 11 further comprising said culture medium configured to facilitate growth of microorganisms introduced to said culture medium, said culture medium being positioned in said tray.

13. The collection system of claim 11 wherein each swab is separated from each adjacent swab in both said lateral direction and said height direction, and wherein said tray is generally flat and planar, and wherein each swab is parallel with a plane of said tray, and wherein said lateral direction is a direction parallel to said plane.

14. A collection system comprising:
a storage tray having an upper surface, the upper surface having a perimeter;

a cover covering the upper surface and sealingly coupled to the perimeter, said cover having a first portion that is attached and retractable from a first area of the upper surface and a second portion that is non-removably attached to a second area of the upper surface;

a plurality of swabs positioned in a plurality of swab receiving recesses separated laterally within said storage tray, wherein at least two of said swab receiving recesses are positioned at different heights within the storage tray; each swab including an absorbent portion configured to collect a sample comprising one or more microorganisms; each swab including a break line along which each swab is predetermined to break;

a storage device positioned in said tray, said storage device being configured to contain a culture medium therein and configured to receive therein at least part of said one or more microorganisms collected by each swab; and a cap positioned in said storage tray, wherein said cap is attachable to said storage device to seal said storage device, wherein said cap includes a sealing component at least partially forming a sealed cavity in which said at least part of said culture medium is positioned, wherein said cap, each swab and said storage device are configured such that after each swab is broken along said break line and positioned in said storage device and said cap is attached to said storage device each swab pierces said sealing component; and each swab and said storage device are sealingly positioned in said tray, and wherein the first portion of said cover is manually manipulable to expose at least part of said plurality of swabs, and wherein the second portion of said cover is not manually manipulable; and wherein the first portion of said cover remains connected to the second portion of said cover when manually manipulated.

15. The system of claim 14 further comprising said culture medium configured to facilitate growth of microorganisms introduced to said culture medium, said culture medium being positioned in said tray, and wherein said cover is manually manipulable to expose said culture medium.

16. The system of claim 14 wherein said cover is manually manipulable to expose said storage device, and wherein said cover is not manually manipulable to expose said absorbent portion of each swab when each swab is in a storage position.

17. The system of claim 14 further comprising said culture medium positioned in said tray, wherein said culture medium is configured to facilitate growth of microorganisms introduced to said culture medium.

18. The system of claim 14 wherein the system is configured such that when said cap is fully secured to said storage device said sealing component is spaced away from a distal inner end of said storage device by a predetermined distance, and wherein each swab is configured to have a length, when broken along said break line, greater than said predetermined distance.

19. The system of claim 14 wherein said cap, each swab and said storage device are configured such that after each swab is broken along said break line and positioned in said storage device and said cap is attached to said storage device each swab has a length greater than a distance between an upper-most inner portion of said cap and a distal inner portion of the storage device such that each swab is deformed between said cap and said storage device.

* * * * *